United States Patent [19]

Beaver

[11] 4,015,597

[45] Apr. 5, 1977

[54] PORTABLE CERVICAL TRACTION APPARATUS

[75] Inventor: Tony J. Beaver, Boise, Idaho

[73] Assignee: Cervical Traction Company, Inc. (Entire), Boise, Idaho

[22] Filed: Oct. 9, 1975

[21] Appl. No.: 621,244

[52] U.S. Cl. .................................. 128/75; 128/87 B
[51] Int. Cl.$^2$ .......................................... A61H 1/02
[58] Field of Search .................. 128/75, 84 C, 87 B, 128/DIG. 23

[56] References Cited

UNITED STATES PATENTS

| | | | |
|---|---|---|---|
| 1,347,913 | 7/1920 | Rink | 128/75 |
| 1,605,578 | 11/1926 | Clark | 128/75 |
| 2,642,864 | 6/1953 | Ward | 128/DIG. 23 |
| 2,706,982 | 4/1955 | Hale et al. | 128/DIG. 23 |
| 3,795,243 | 3/1974 | Miller | 128/75 |

Primary Examiner—John D. Yasko
Attorney, Agent, or Firm—Clarence A. O'Brien; Harvey B. Jacobson

[57] ABSTRACT

A support frame for embracing the upper portion of the shoulders of a person to undergo cervical traction is provided and the frame includes inverted transversely spaced aligned U-shaped opposite side members having an upper transverse brace extending between and secured to the bight portions of the side members as well as lower braces extending between and secured to corresponding lower leg portions of the inverted U-shaped opposite side members. Further, the lower ends of the legs of each side member are rigidly interconnected by means of a support brace extending therebetween and the lower terminal ends of the legs of each side member project downwardly below the support brace. A pair of downwardly opening generally semi-cylindrical shoulder plates are secured between the lower terminal ends of the legs of the side members and the central portions of the downwardly opening shoulder plates are disposed immediately beneath and secured to the central portions of the corresponding support braces. The central portion of the upper transverse brace supports a block and tackle assembly which depends downwardly therefrom and supports a head harness at its lower end and the block and tackle assembly includes a free line end which extends outwardly from the upper portion of the block and tackle assembly and through a pulley block supported from the bight portion of one of the inverted U-shaped opposite side members. The free end of the line is wound about a winding member journaled from the lower portion of he same opposite side member.

3 Claims, 5 Drawing Figures

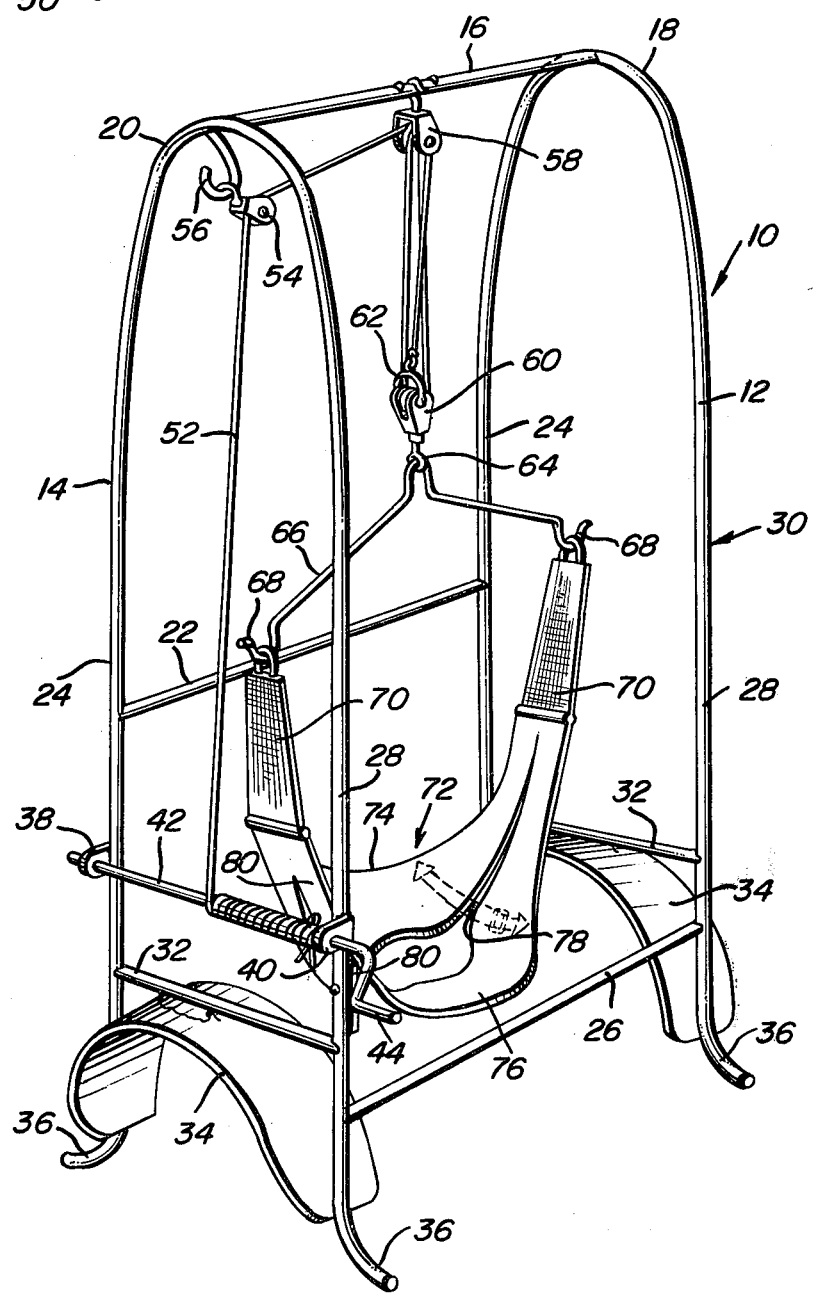

PORTABLE CERVICAL TRACTION APPARATUS

BACKGROUND OF THE INVENTION

Various forms of devices for applying cervical traction have been heretofore designed and examples of such prior known devices are disclosed in U.S. Pat. Nos. 2,642,864, 2,706,982, 3,605,736 and 3,795,243.

However, some previously known cervical traction devices have not included means whereby cervical traction may be adjusted and maintained by the person to undergo cervical traction. In addition, most apparatus for applying cervical traction is reasonably cumbersome and heavy as well as somewhat complex in use. Further, various other forms of previously known cervical traction are not portable and thereby not readily usable by the patients themselves at home whenever cervical traction is needed and are somewhat complex in structure so as to thus require periodic maintenance. In addition, some previously known cervical traction devices may not readily be utilized by patients in a manner resulting in little pain or discomfort and certain more complex cervical traction devices are not readily adjustable for use on persons of different sizes.

BRIEF DESCRIPTION OF THE INVENTION

It is accordingly the main object of this invention to provide a portable cervical traction device which may be used by a patient at home and without the help of others in order to apply the required cervical traction in a comfortable manner.

Another object of this invention is to provide a cervical traction apparatus which requires little instruction in use and which may therefore be quickly mastered by a person requiring cervical traction.

Another important object of this invention is to provide a cervical traction apparatus which is wholly portable and which is worn by the patient when in use thereby enabling the patient to maintain his mobility.

Still another object of this invention is to provide a cervical traction apparatus which requires little maintenance and is fully adjustable to size of the individual to undergo cervical traction.

A final object of this invention to be specifically enumerated herein is to provide an apparatus in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the cervical traction apparatus of the instant invention;

FIG. 5 is a fragmentary perspective view illustrating the manner in which the free end of the tension line is attached to the winding member portion of the traction apparatus.

DETAILED DESCRIPTION OF THE INVENTION

Figures 3, 4:
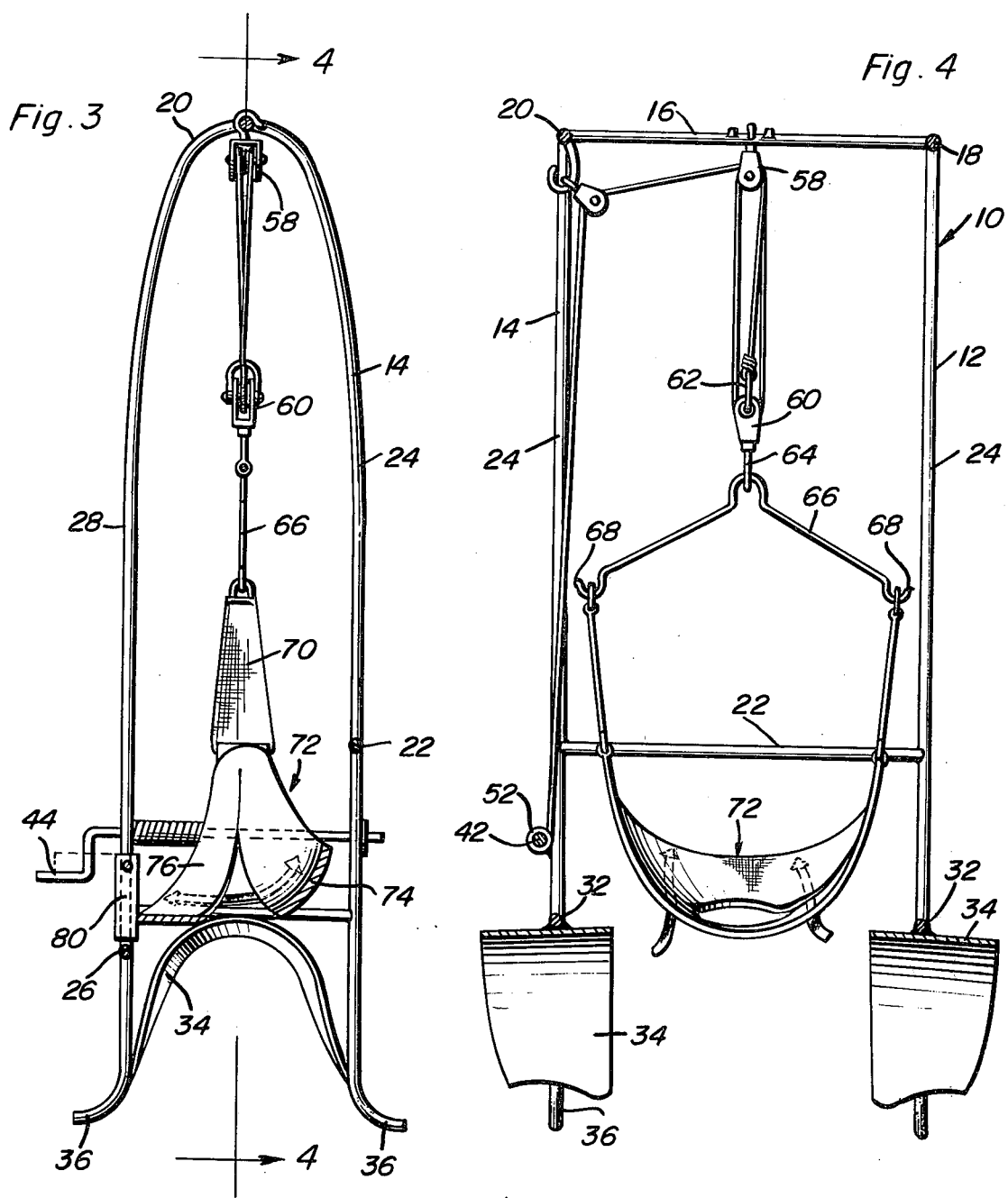
FIG. 3 is a vertical sectional view taken substantially upon the plane indicated by the section line 3—3 of FIG. 2.
FIG. 4 is a vertical sectional view taken substantially upon the plane indicated by the section line 4—4 of FIG. 3.
Figure 2:
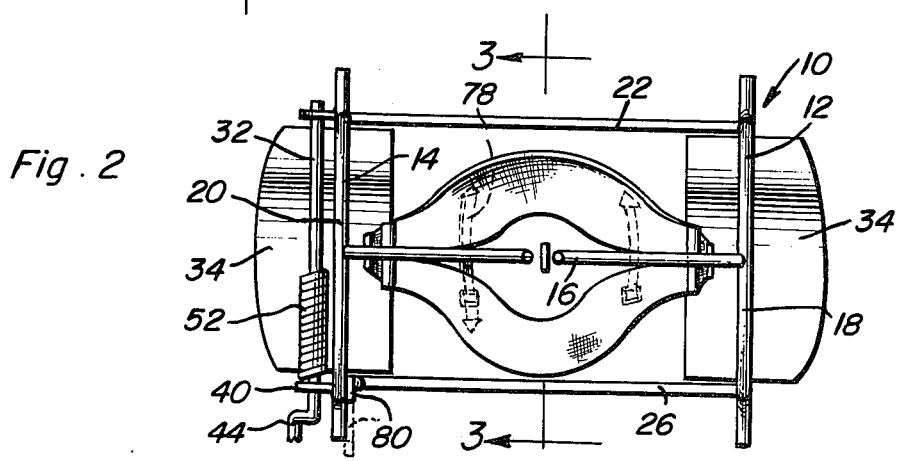
FIG. 2 is a top plan view of the assemblage illustrated in FIG. 1 and illustrated on somewhat of a reduced scale.

Referring now more specifically to the drawings, the numeral 10 generally designates the traction apparatus of the instant invention. The apparatus 10 includes a pair of transversely aligned inverted U-shaped opposite side members 12 and 14 interconnected at their upper ends by means of an upper transverse brace 16 extending between the bight portions 18 and 20 of the side members. In addition, a first lower brace 22 extends between and is secured to corresponding depending legs 24 of the U-shaped members 12 and 14 and a second lower brace 26 is secured between the corresponding legs 28 of the members 12 and 14. The aforementioned components of the apparatus 10 together form a main frame referred to in general by the reference numeral 30.

The frame 30 additionally includes a pair of support braces 32 extending and secured between each pair of corresponding legs 24 and 28 at elevations spaced above the lower end portions of the legs 24 and 28 and a pair of downwardly opening semi-cylindrical shoulder plates 34 are disposed between and secured to the lower ends of each pair of corresponding legs 24 and 28 with the upper portions of the shoulder plates 34 underlying and secured to the corresponding support braces 32, the lower terminal ends of the legs 24 and 28 including outwardly curving lower terminal ends 36.

A pair of outstanding apertured mounting flanges 38 and 40 are secured to the legs 24 and 28 of the side member 14 and the flanges 38 and 40 are equipped with aligned bores through which opposite end portions of a winding shaft 42 are journaled, the end of the shaft 42 journaled through the flange 40 being equipped with a crank 44. From FIGS. 1 and 5 of the drawings it may be seen that a disk 46 is mounted on the winding shaft 42 immediately inwardly of the bracket 40 and that the disk 46 is removably keyed in position on the shaft 42 by means of a diametric cotter pin 48. The disk 46 has an outstanding apertured flange 50 mounted thereon and one end of a tension line 52 is secured to the flange 50 with the adjacent portion of the line 52 wound about the shaft 42. The line 52 extends upward from the shaft 42 and through a single pulley block 54 suspended from a hook 56 dependingly anchored to the bight portion 20. The line 52 then passes over one of the pulleys of a double pulley block 58 suspended from the mid-portion of the upper transverse brace 16, passes downwardly beneath the pulley of a single pulley block 60 disposed below the pulley block 58 and then upwardly over the second pulley of the pulley block 58 before extending downwardly again toward and being anchored to the single pulley blocks 60, as at 62.

The lower single pulley block 60 includes a dependingly supported support eye 64 from which a head harness supporting frame 66 is supported. The frame 66 includes downwardly divergent opposite side arms defining hook portions 68 at their free ends and the opposite side straps 70 of a head harness referred to in general by the reference numeral 72 have their upper ends removably supported from the hook portions 68.

The head harness 72 includes a pair of spaced strap portions 74 and 76 adapted to pass in back of the base of the head and beneath the chin of the user. The end portions of the straps or strap members 74 and 76 are interconnected by strap members 78. Furthermore, the leg 28 of the frame side member 14 includes a latch 80 shiftably supported therefrom and which may be engaged with the crank 44 to retain the shaft 42 in adjusted rotated position.

In operation, the frame 30 is placed over the shoulders of the user after the head harness 72 has been placed over the user's head. Then, the strap portions 70 are engaged with the hooks 68 and the crank 44 may be orbited to cause rotation of the winding shaft 42 and the line 52 to wind on the shaft 42 resulting in the support frame 66 and the head harness 72 being elevated relative to the upper transverse brace 16. This, of course, will apply cervical traction to the user. If it is desired, the user may maintain the desired amount of cervical traction by holding the crank 44 in position. However, if cervical traction is to be applied over longer periods, the latch 80 may be shifted into operative position engaged with the crank 44 in order to maintain the winding shaft 42 against rotation in a direction which would cause the line 52 to become slack.

The shoulder plates 34 may, of course, be padded and it is to be noted that a person to undergo cervical traction may readily apply the apparatus 10 to himself without the aid of others. Furthermore, the traction apparatus is of lightweight construction and yet sturdy and may therefore be transported from one location to another. Furthermore, the construction of the traction apparatus 10 is such that it may be applied to persons of various sizes and if it is to be utilized on very small persons it may be constructed on a slightly smaller scale.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination, a pair of upstanding generally parallel and inverted U-shaped opposite side frame portions disposed and spaced side-by-side relation, each of said frame portions including front and rear legs interconnected at their upper end portions by means of a curved bight portion extending therebetween, said frame portions being spaced apart at their lower ends a distance less than shoulder width but greater than head width, a front to rear extending brace rigidly secured between the lower end portions of the front and rear legs of each frame portion, an upper horizontal brace member extending between and rigidly anchored to said bight portions, transverse braces extending between and rigidly secured to each pair of corresponding front and rear legs intermediate the upper and lower ends thereof, a downwardly concave arched shoulder support received and extending between and rigidly secured to the lower end portions of the legs of each frame portion, said front to rear extending braces closely overlying and being secured to the longitudinal mid-portions of said shoulder supports, a block and tackle assembly depending downwardly from a central portion of said upper horizontal brace member and supporting a head sling therefrom, said block and tackle including a pull line free end portion, a winding member journaled from a lower portion of one of said opposite frame portions, the free end portion of said pull line being attached to said winding member for winding thereon, the upper end portion of said one opposite side frame portion including anti-friction guide means supported therefrom with which an intermediate portion of said winding member free end portion extending between said block and tackle and said winding member is guidingly engaged for longitudinal shifting relative thereto.

2. The combination of claim 1 including latch means supported from said one frame portion and releasably engageable with said winding member for retaining the latter in adjusted rotated positions on said one side frame portion.

3. The combination of claim 1, wherein said head sling includes a pair of generally parallel strap portions having corresponding ends secured together and mid-portions which are free of direct connection with each other, corresponding ends of said mid-portions having flexible strap means extending and secured therebetween.

* * * * *